(12) United States Patent
Dunne

(10) Patent No.: US 6,198,956 B1
(45) Date of Patent: Mar. 6, 2001

(54) HIGH SPEED SECTOR SCANNING APPARATUS HAVING DIGITAL ELECTRONIC CONTROL

(75) Inventor: Shane Denis Dunne, Kingston (CA)

(73) Assignee: OTI Ophthalmic Technologies Inc., Downsview (CA)

(*) Notice: Subject to any disclaimer, the term of this patent is extended or adjusted under 35 U.S.C. 154(b) by 0 days.

(21) Appl. No.: 09/409,095

(22) Filed: Sep. 30, 1999

(51) Int. Cl.[7] .................................................. A61B 5/00
(52) U.S. Cl. ...................... 600/407; 600/446; 600/459; 73/633
(58) Field of Search .................... 600/437, 444–446, 600/459, 462–467; 73/633; 310/14–15, 23–24; 318/119, 128; 361/152–154; 359/198–199, 212–213

(56) References Cited

U.S. PATENT DOCUMENTS

| | | |
|---|---|---|
| 4,092,867 | 6/1978 | Matzuk . |
| 4,732,156 | 3/1988 | Nakamura . |
| 4,785,816 * | 11/1988 | Dow et al. ............................ 600/446 |
| 4,787,247 * | 11/1988 | Wochinich et al. .................. 600/446 |
| 4,974,918 * | 12/1990 | Delache et al. ....................... 350/6.6 |
| 5,159,931 | 11/1992 | Pini . |
| 5,357,963 * | 10/1994 | Mayol et al. ......................... 600/446 |
| 5,373,845 | 12/1994 | Gardineer et al. . |
| 5,454,371 | 10/1995 | Fenster et al. . |
| 5,562,095 | 10/1996 | Downey et al. . |
| 5,647,367 | 7/1997 | Lum et al. . |
| 5,701,901 | 12/1997 | Lum et al. . |
| 5,754,327 * | 5/1998 | Masotti et al. ....................... 359/198 |
| 5,827,266 * | 10/1998 | Harel et al. ........................... 606/13 |
| 5,842,473 | 12/1998 | Fenster et al. . |
| 6,066,998 * | 5/2000 | Trumper et al. ..................... 335/229 |

* cited by examiner

Primary Examiner—Francis J. Jaworski
(74) Attorney, Agent, or Firm—Marks & Clerk

(57) ABSTRACT

An ultrasonic scanner has a housing, an ultrasonic transducer mounted within the housing for back-and-forth motion about a pivot, a permanent magnet affixed to the rear of the transducer, and electromagnetic means to effect movement of the transducer/magnet assembly. The electromagnetic means comprises two or more longitudinally mounted electromagnets, and optionally two radially mounted permanent magnets which serve as decelerating buffers. Electrical means are provided for energizing the transducer and receiving signals therefrom. Digitizing means are provided to convert the received signals to digital form. Sequential control means are provided to energize the electromagnet coils in a programmed sequence, and furthermore to synchronize transducer motion, periodic energization of the transducer, and digitization of signals received from the transducer. Display means are provided to present the signals received by the transducer to an operator, in the form of a time-varying tomographic image. More generally, a scanning device is provided having electromagnets co-acting with a permanent magnet mounted on a rocker, and coupled with a source and detector for high energy signals, so that a sweeping motion of the rocker can be effected, and an image of the target tissue may be reconstructed.

19 Claims, 10 Drawing Sheets

HIGH SPEED SECTOR SCANNING APPARATUS HAVING DIGITAL ELECTRONIC CONTROL

FIELD OF THE INVENTION

This invention relates to ultrasonic scanning apparatus wherein an ultrasonic transducer is mounted for continuous reciprocating motion, with motive force provided by electromagnetic means under digital electronic control. Preferably, the reciprocating transducer assembly is disposed within a hand-held probe. Also preferably, the working end of the probe (from which ultrasonic signals are emitted and received by the transducer) has a diameter less than 20 millimeters, to facilitate use in scanning the living human eye for ophthalmic diagnosis purposes.

BACKGROUND OF THE INVENTION

Ultrasonic imaging, also called echography or B-mode ("brightness mode") ultrasound, involves use of an ultrasonic transducer which repeatedly emits pulses of high-frequency sound and receives the resulting echo signals. A focused beam of sound is normally used, and various means are employed to sweep this beam repeatedly through a range of directions. Electronic processing of the received echo signals, synchronized to the movement of the beam, results in formation of a video image (normally cross-sectional) of structures (such as human tissue) in the beam's path.

For clarity of exposition, the following discussion refers specifically to the medical diagnostic imaging situation in which the target of the ultrasonic imaging system is tissue in a living human patient. It should be realized that ultrasonic scanning is also used in other applications including non-human (veterinary or in vitro tissue sample) biological imaging, and also non-biological imaging applications (non-destructive materials testing), and that the present invention applies without limitation to all such ultrasonic imaging applications.

In ultrasonic scanners for medical diagnostic imaging, the transducer and beam-sweeping components are normally assembled in the form of a hand-held probe connected to the rest of the imaging system by means of a cable. In the following, the term "probe" will be used generically to refer to the transducer and beam-scanning assembly, though it should be realized that not all ultrasonic scanning systems will have or need a physically distinct probe component.

Because the sound frequencies used in ultrasonic imaging are effectively blocked by air, it is necessary to acoustically couple the transducer to the target under investigation via one or more acoustically conductive media. Coupling media must be chosen carefully, to ensure that the effects of sound reflection and refraction occurring at media interfaces do not unduly compromise the imaging capabilities of the system. In practice, the problem of coupling is addressed in one of three ways:

1. Liquid bath. The transducer and target are immersed in a liquid coupling medium such as water or sterile saline solution. This technique is rarely used in clinical scanning applications.
2. Sealed transducer chamber. The transducer is sealed within a liquid-filled chamber within the probe, with a solid "acoustic window" through which the imaging beam can pass.
3. Acoustic coupling gel. Several water-based gel media are now on the market, which provide a convenient means to couple a probe's acoustic window to the surface of target tissue.

Many techniques for sweeping the sound beam are known, but as at the date of filing of this application, there are two main approaches which are in common use. In the mechanical sector-scan approach, a transducer is mechanically oscillated about a pivot, causing the sound beam to sweep through a sector. Acoustic coupling to target tissue may be achieved either by method 1 above, or more commonly, a combination of methods 2 and 3. In the electronic transducer array approach, a fixed array of multiple transducer elements is used, and the sound beam is formed, focused, and swept entirely electronically. Because there is no transducer movement, coupling method 2 above is unnecessary; method 3 alone is sufficient.

The electronic transducer array approach generally provides greater speed, precision and repeatability of sound beam motion than the mechanical sector-scan approach, and hence today the array approach is widely used. However, the array approach, which requires one signal processing channel (e.g. impedance matching and filtering, signal conditioning and amplification, and sometimes digitization) per array element, is inherently more expensive than the mechanical sector scanning approach, and so the mechanical sector scanning approach is still used. In the field of ophthalmology, for example, mechanical sector scanners are still used exclusively. There thus remains a need to advance the state of the art with respect to the mechanical sector scan approach.

So-called annular array transducers, which consist of a small number of concentric ring-shaped transduction elements, may be used in place of a single-element transducer in a mechanical sector scanning apparatus. These devices permit electronic control of sound beam focusing, but not direction. Because the number of transduction elements is small (e.g. three to eight), the cost premium associated with annular array transducers is slight compared with that of a fall electronic array beam sweeping system.

In this application, the term "transducer" refers equally to either a single element transducer or an annular array transducer.

Ultrasonic scanning and image formation can occur quite rapidly, which makes possible dynamic imaging in the presence of motion, e.g. of the living fetus in utero, of the tissues in the eye, or in the course of interventional medical procedures such as catheterization or laparoscopic surgery. The fidelity with which continuous motion can be represented in the live ultrasonic image depends primarily on how rapidly the sound beam can be scanned across the field of view, and on how precisely and repeatably the scanning motion can be controlled.

Purely mechanical means of oscillation, with or without use of magnetic elements on some of the moving members to transfer force across a gap, exhibits a number of disadvantages. The mechanical drive assembly adds substantially to the size and weight of the imaging probe, and to achieve precisely controlled motion it is necessary to augment the mechanical system with a positional sensor and to employ closed-loop feedback control methods in the control system. Addition of the positional sensor adds yet further to the size, weight, and complexity of the probe, while the need for closed loop feedback control adds to the complexity of the control system.

However, motive force may also be applied by means of magnetic forces established between fixed electromagnets, energized with time-varying electric current, and a single permanent magnet affixed to a rotating transducer assembly. Generally, in all of these cases the magnetic oscillator mechanism follows the general principle of a galvanometer, i.e., a magnetic field is established in a fixed stator member, with the magnetization vector substantially at right angles to that of a permanent magnet affixed to a pivoted rocker member. The magnet in the rocker is thus subjected to magnetic torque forces which cause it, and the rocker, to tilt or rotate so as to reduce the angle between the two magnetic vectors. Periodically reversing the direction of the stator field, by passing an alternating current through the one or more electromagnet coils in the stator assembly, thus results in a periodically reversing torque applied to the rocker, and in consequence causes the rocker to oscillate.

In practice, such galvanometer-like mechanisms cannot transfer appreciable amounts of mechanical energy, because of the inverse square relationship between magnetic force and distance. As the rocker magnet tilts away from the center position, it moves further from the stator magnet poles, dramatically reducing the torque efficiency of the system and making it harder to apply the reverse torque required to tilt the rocker back in the opposite direction. Such a system is rather like a heavy weight balanced atop a rod held in the hand; provided the rod does not tip very far from the vertical, small movements of the hand suffice to keep it stably aloft, but the range of controllable motion is very small.

The present invention solves the torque efficiency problems by using a system of many digitally switched stator electromagnet coils, which permit periodic alteration of the magnetic field vector while maintaining a small and little-varying gap between the currently active stator poles and a permanent magnet in the rocker, and furthermore solves the problem of stability at higher operating speeds by providing additional permanent magnets affixed to the stator near the extremes of the rocker's oscillatory motion, oriented so as to repel the permanent magnet in the rocker, causing it to spring back in the opposite direction.

DESCRIPTION OF THE PRIOR ART

Motive force in mechanical sector scanning devices frequently involves use of an ordinary rotating electric motor plus some form of mechanical linkage to transform rotational motion to back-and-forth oscillatory motion of the transducer. U.S. Pat. No. 5,357,963 issued to LUM et al. discloses a variation of the standard linkage in which the force of attraction between two permanent magnets is used to effect transfer of motive force through the wall of a sealed fluid-filled transducer chamber. Also, NAKAMURA et al. U.S. Pat. No. 4,732,156 discloses a similar concept in which the sealed transducer chamber and magnetic linkage are disposed at the end of a flexible mechanical coupling shaft to facilitate insertion of the whole assembly into a body cavity, and the sound beam from a fixed transducer is caused to scan by means of a rotating mirror.

Still further MATZUK U.S. Pat. No. 4,092,867 discloses two mechanisms in which motive force may be applied by means of magnetic forces established between fixed electromagnets. Here, magnetic means are provided for moving a transducer in a predetermined path. The scanner is servo-controlled and is provided with position sensing means for determining a position of the transducer within the predetermined path; and there is a feedback circuit provided to adjust the transducer position responsive to feedback signals which indicate the existence of a departure from the desired transducer position. Matzuk explicitly acknowledges the need for an active feedback control system to maintain stable motion. This results in a probe mechanism which is substantially larger than the size of the ultrasonic transducer itself.

LUM et al. U.S. Pat. No. 5,647,367 discloses an ultrasonic probe which is particularly intended for imaging tissues from inside a body cavity of a patient. Here, an ultrasonic beam emitting assembly has a pivotable part which is moveable and which is operatively connected to a housing. The pivotable part can have an ultrasonic transducer mounted on it, or a reflector, and in either case, it will sweep ultrasonic energy over a selected angle. However, the magnetic oscillator mechanism generally follows the principal of a galvanometer having a magnetic field which is established in a fixed stator member, with the magnetization vector being substantially at right angles to that of a permanent magnet affixed to the pivoted rocker member.

A further patent issued to LUM et al., U.S. Pat. No. 5,701,901, teaches a similar structure, where the support is a silicone-containing support for a transducer, and where there is an electro-magnetic drive which is located near the transducer assembly to act on a ferromagnetic material on the transducer assembly resulting in pivotal motion of the transducer on the support arms provided therefor. Both of the Lum et al. patents noted immediately above acknowledge the requirement for an active feedback control system to maintain stable motion, and address the problem in a limited way by proposing a specially fabricated rocker having near-zero mass, and driven by a stator electromagnet having very much larger relative size. Once again, this results in a probe mechanism which is substantially larger than the size of the ultrasonic transducer itself.

PINI U.S. Pat. No. 5,159,931, FENSTER et al. U.S. Pat. No. 5,454,371, DOWNEY et al. U.S. Pat. No. 5,562,095, and a further FENSTER et al. U.S. Pat. No. 5,842,473, all describe apparatus by which three-dimensional images may be assembled from multiple planar echographic images. Image fidelity with such three dimensional ultrasonic image acquisition and reconstruction techniques also depends strongly on the speed, precision and repeatability of the sound beam scanning; far more strongly, in fact, than in the case of dynamic two-dimensional imaging.

SUMMARY OF THE INVENTION

While, in general, the present discussion is directed more to ultrasonic transducers than others, it will be noted that ultrasonic transducers are not the only high frequency energy transducers which can be utilized in various physical embodiments of the present invention, as described in greater detail hereafter.

In its broadest sense, the present invention provides a high speed sector scanning apparatus having digital control. The apparatus of the present invention comprises a frame, a rocker mounted on an axle near a first end of the frame, a first permanent magnet mounted at the end of the rocker, at least two electromagnets mounted in the plane swept by the first permanent magnet a flux return path mounted in the frame, digital electrical control means, a source of high frequency energy, and a detector physically mounted so as to interact with the rocker and so as to detect and receive reflected high frequency energy.

The rocker is mounted on its axle and is adapted for oscillatory movement about a rocker axis which is defined by that axle through a range of up to 180°, and typically through a range of from 10° up to 95°. The first permanent magnet is mounted at the end of the rocker which is remote from the first end of the frame, so as to define a locus which is located in a plane swept by the permanent magnet during oscillatory movement of the rocker.

There are at least two electromagnets, each of which comprises a coiled wire wound on an elongated magnetic core. The at least two electromagnets are mounted in the plane which is swept by the first permanent magnet, and each of the at least two electromagnets is constructed so as to have a first end of its magnetic core extending towards the locus defined by movement of the first permanent magnet. Magnetic field reaction will occur between the first permanent magnet and at least one of the at least two electromagnets when electric power is selectively applied to that at least one electromagnet at any instant in time.

As noted, there is a flux return path which is mounted in the frame, and which is magnetically connected to the ends of the at least two electromagnets.

The digital electrical control means selectively applies electric power to at least one electromagnet at any instant in time, and sequentially applies power to others of the at least two electromagnets over a period of time. Thus, magnetic field reaction will sequentially occur between the first permanent magnet and a selected at least one electromagnet, so as to cause oscillatory movement of the rocker about the rocker axis as the first permanent magnet moves in its defined locus in the swept plane.

A source of high frequency energy is physically mounted so as to interact with the rocker, so that energy is transmitted away from the rocker along a transmission axis of the rocker, which is orthogonal to the rocker axis. The detector is physically mounted so as to interact with the rocker and to detect and receive selected high frequency energy returning from the target material, either through reflection or any other interaction mechanism, such as fluorescence.

Normally, apparatus in keeping with the present invention will further include a pair of permanent rebound magnets which are mounted in the frame so that one of the pair of permanent rebound magnets is mounted at each end of the locus defined by the first permanent magnet which is mounted on the rocker. Thus, a magnetic repulsion reaction will occur between the first permanent magnet and either of the two rebound magnets, each time the first permanent magnet approaches the respective one of the permanent rebound magnets during oscillatory movement of the rocker.

Generally, the source of high frequency energy and the detector are mounted on the rocker. They may be an ultrasonic transducer, but as well the source of high frequency energy may be laser diodes, lamps, light emitting diodes, and superluminescent diodes.

In some embodiments of the present invention, the source of high frequency energy and the detector are physically mounted within the frame. Moreover, there may be mounted within the frame a curved reflector, mounted near the first ends of the at least two electromagnets, together with at least one lever arm which extends from the rocker axis of the rocker and having the first permanent magnet mounted on the lever arm which is remote from the rocker axis. Thus, in such an embodiment, energy which is transmitted from the source of high frequency energy is transmitted towards the curved reflector, and is then re-transmitted from the curved reflector outwardly from the apparatus past the first end of the frame, towards the object to be scanned by the apparatus.

In such an embodiment as that described immediately above, the reflector may be a sound reflector, or it may be a mirror.

In yet another embodiment of the present invention, the source of high frequency energy may be a light source which is physically mounted within the frame; and the light source may be such as a laser diode, a lamp, a light emitting diode, a superluminescent diode, or a light fiber connected to a light source which may, itself, be a laser diode, a lamp, a light emitting diode, or a superluminescent diode. In any event, a planar mirror is mounted on the rocker at the end of the rocker which is remote from the first permanent magnet, and the source of high frequency energy is mounted within the frame so as to be directed at the planar mirror. The planar mirror is, of course, mounted so as to be orthogonal to the axis of transmission of the rocker. Here, the detector is physically mounted within the frame so as to interact with the rocker, and so as to detect and receive reflected high frequency energy being reflected back to the planar mirror from an object being scanned by the apparatus.

In yet another embodiment of the present invention, the source of high frequency energy may be a source of broad coverage illumination. Here, the detector is one which will detect high frequency energy from that source of broad coverage illumination as that high frequency energy is reflected back to the apparatus from an object being scanned by the apparatus. In that case, the detector is physically mounted on the rocker.

In the embodiment described immediately above, a typical source of high frequency energy which provides broad coverage illumination may be a Xenon lamp.

A further embodiment of the present invention provides for the source of high frequency energy being a light source which is physically mounted within the frame, and mounted on the rocker. In that case, the detector would be a stationary broad coverage detector; such a detector might a photomultiplier tube.

Generally, the present invention provides an apparatus where there may be any number of electromagnets mounted in the frame; however, in general there will be from three to six electromagnets mounted within the frame.

In many instances, the electric power which is sequentially applied by the digital control means to each electromagnet is applied to one electromagnet at a time. Then, electric power is next applied by the digital control means to an electromagnetic which is adjacent to the last electromagnet to have had electric power applied to it, each time the sequence of the application to the electromagnets changes.

Alternatively, where there are at least three electromagnets, the electric power may be applied sequentially by the digital control means to pairs of adjacent electromagnets. Thus, in successive steps, the sequence of application of electric power to the electromagnets is such that one of the respective pairs of electromagnets having electric power applied thereto is the same electromagnet.

Especially when the source of high frequency energy is an ultrasonic transducer, the apparatus will include an acoustic window at the first end thereof; and, of course, the acoustic window is acoustically transparent to the high frequency ultrasonic energy within the operating frequency range of the ultrasonic transducer. The rocker, the transducer, the detector, and the first ends of the at least two electromagnets are sealed in a liquid-tight chamber, which is defined at one end by the acoustic window. The liquid-tight chamber is filled with a liquid which is acoustically transparent to high frequency energy at least at the operating frequency of the ultrasonic transducer.

A feature of the present invention is that it may comprise a mechanism which is mechanically coupled to the frame, for selectively translating the frame under controlled conditions, from one location to another. For example, the mechanism which is mechanically coupled to the frame may selectively rotate the frame under controlled conditions about a longitudinal axis of the frame.

Still further, the mechanism for selectively translating the frame under controlled conditions from one location to another may be a mechanism which will selectively tilt the frame under controlled conditions about a tilt axis. In that case, each of the plane which is swept by the first magnet, and the transmission axis of the rocker, will be tilted about that tilt axis.

Finally, the present invention may find itself being employed in an ultrasound tomographic imaging system where the ultrasonic transducer is sealed in a liquid-tight chamber within the frame, and functions together with ultrasound image reconstruction circuitry and display means, for displaying reconstructed ultrasound images.

BRIEF DESCRIPTION OF THE DRAWINGS

The novel features which are believed to be characteristic of the present invention, as to its structure, organization, use and method of operation, together with further objectives and advantages thereof, will be better understood from the following drawings in which a presently preferred embodiment of the invention will now be illustrated by way of example. It is expressly understood, however, that the drawings are for the purpose of illustration and description only and are not intended as a definition of the limits of the invention. Embodiments of this invention will now be described by way of example in association with the accompanying drawings in which.

DETAILED DESCRIPTION OF THE PREFERRED EMBODIMENTS

In most embodiments of the present invention, a permanent magnet is affixed to the rear of a pivoted rocker assembly containing an ultrasonic transducer or other source of high frequency energy. The rocker pivots within a stator assembly in which is mounted a series of electromagnet coils, and optionally a pair of permanent magnets at the extreme points of the rocker's motion. The whole is contained within a probe housing having an acoustically transparent window at the end closest to the transducer, through which the emitted and received sound pulses travel.

Figure 1:
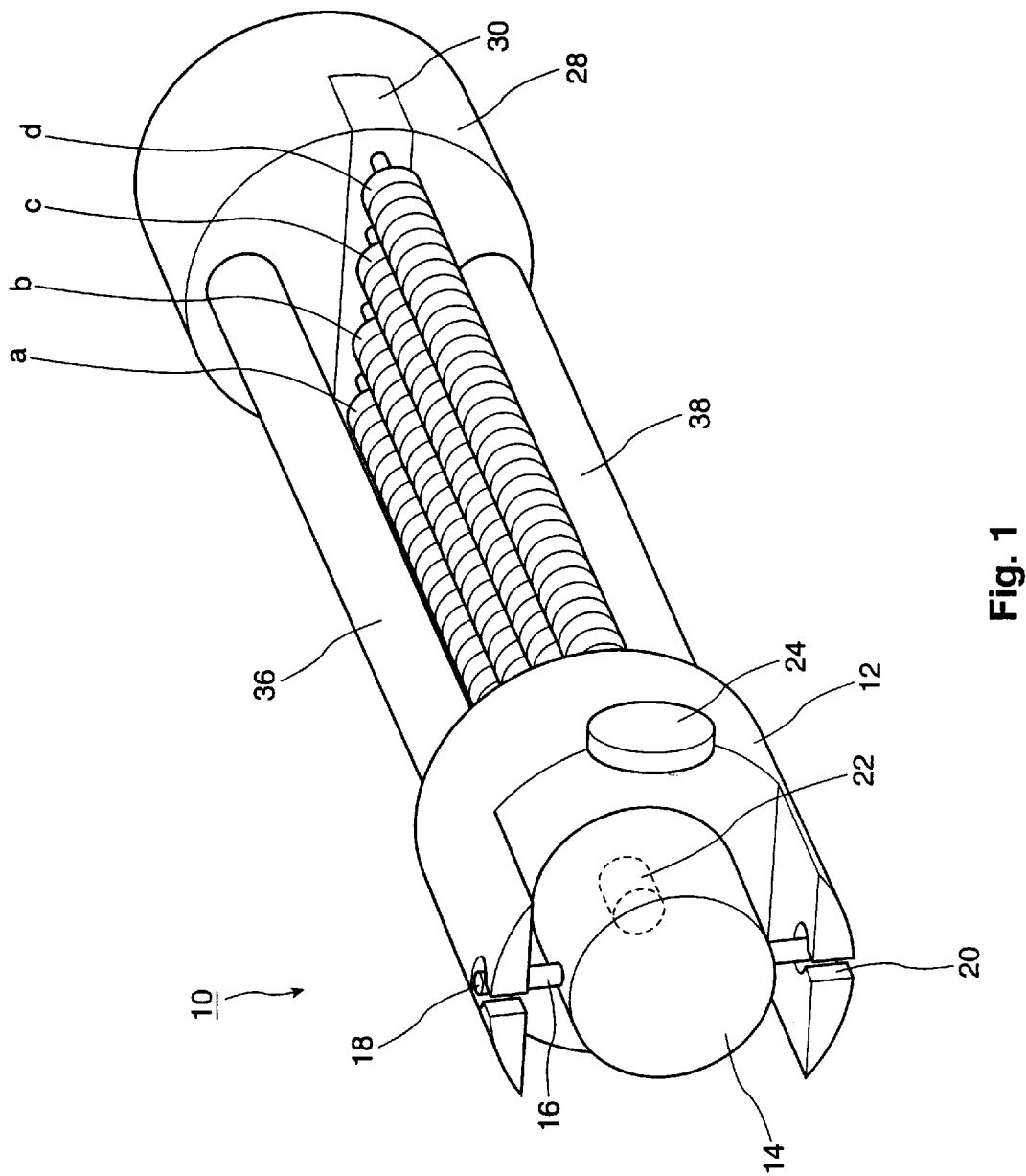
FIG. 1 is a simplified perspective of the basic working elements of a high speed sector scanning apparatus in keeping with the present invention.
Figure 2:
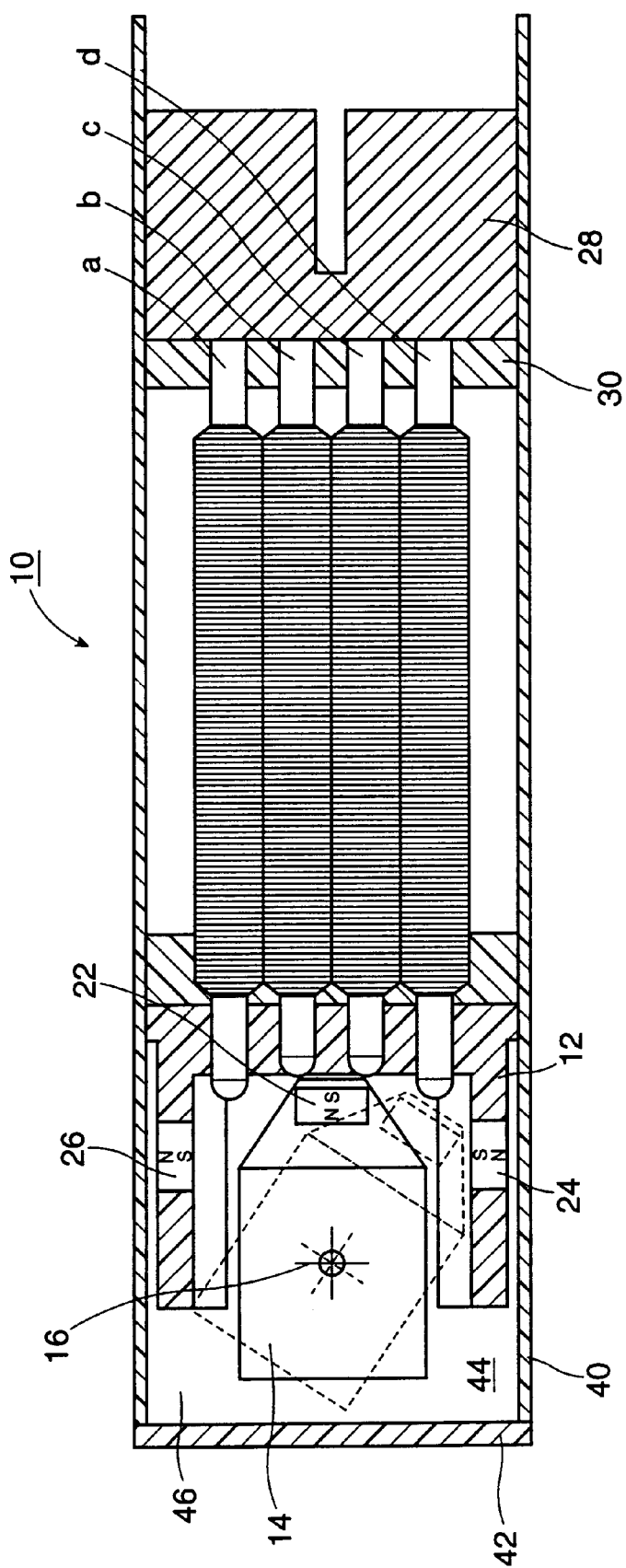
FIG. 2 is a horizontal plan view through a central section of the scanner of FIG. 1.

In operation, the electromagnet coils are energized in alternating sequence. For example, with four coils as shown in FIGS. 1 and 2, and as described in greater details hereafter, the sequence could be, for example, a, b, c, d, c, b, a, etc.; or a+b, b+c, c+d, b+c, a+b, etc. The permanent magnet in the rocker is attracted to the energized coil or coils, and hence oscillates about the pivot. At high speed, the tendency of the rocker to overshoot the outermost electromagnet poles is counteracted by the local repulsion forces established by two permanent magnets mounted in the stator assembly. At lower speeds, the outermost electromagnets may be strong enough to reverse the rocker direction, in which case these "rebound" magnets are not needed.

The alternating sequence of electromagnet coil energization is established by a digital electronic switching system, typically controlled by a computer or microprocessor. Provided sufficient effort is made to control friction (e.g. ball or jewel bearings at the pivot) and fluid drag (e.g. suitably hydrodynamic rocker shape), inertial forces will dominate, making the rocker motion highly predictable and repeatable. Hence rapid, precise and repeatable oscillating motion of the transducer maybe achieved without the need for direct sensing of the instantaneous transducer position, and/or the use of closed-loop feedback techniques, which would adjust the coiled energizing sequence to correct measured departures from the ideal position.

Following widely known principles of digital electronics, the operation of the electronic switching system (and, hence, the rocker motion), may be synchronized with other processes required in an ultrasonic imaging scanner, e.g. energization of the ultrasonic transducer, reception of received ultrasonic signals, and image reconstruction and display. Thus, a dynamic two-dimensional ultrasound tomographic imaging system may be implemented with a minimum of components, and with a very small and simple probe having but one moving part.

Furthermore, the transducer motion may be further synchronized with a suitable mechanism for translating, tilting, rotating, etc., the entire sector-scan mechanism, to facilitate capture of multiple two-dimensional planar cross section images for assembly into a composite three-dimensional image.

This basic design admits a number of useful variations, including without limitation the following:

1. A fixed curved acoustic reflector may be added to alter the scanning path of the sound beam, in particular to yield a scanning path compatible with ultrasonic imaging of the anterior segment of the eye.

2. Instead of disposing the transducer within the moving rocker, the rocker may instead contain an acoustic reflector to reflect and sweep the sound beam emitted by a fixed ultrasonic transducer.

3. In any of the variations of the base design, the ultrasonic transducer may be replaced by another high frequency energy source and/or detector, in particular an optical source such as a semiconductor diode laser or superluminescent diode, or one end of a flexible optical fiber coupled to a fixed energy source and/or detector at the far end of the fiber.

4. Although in ultrasonic imaging it is most common to utilize a single transducer for emission and detection of sound, in optical imaging either the source or the detector device may be fixed. For example, with respect to variation #3 above, the light beam from a semiconductor diode type light source could be swept across the target area while reflections are received by a fixed, wide-field detector such as a photomultiplier tube.

Figure 3:
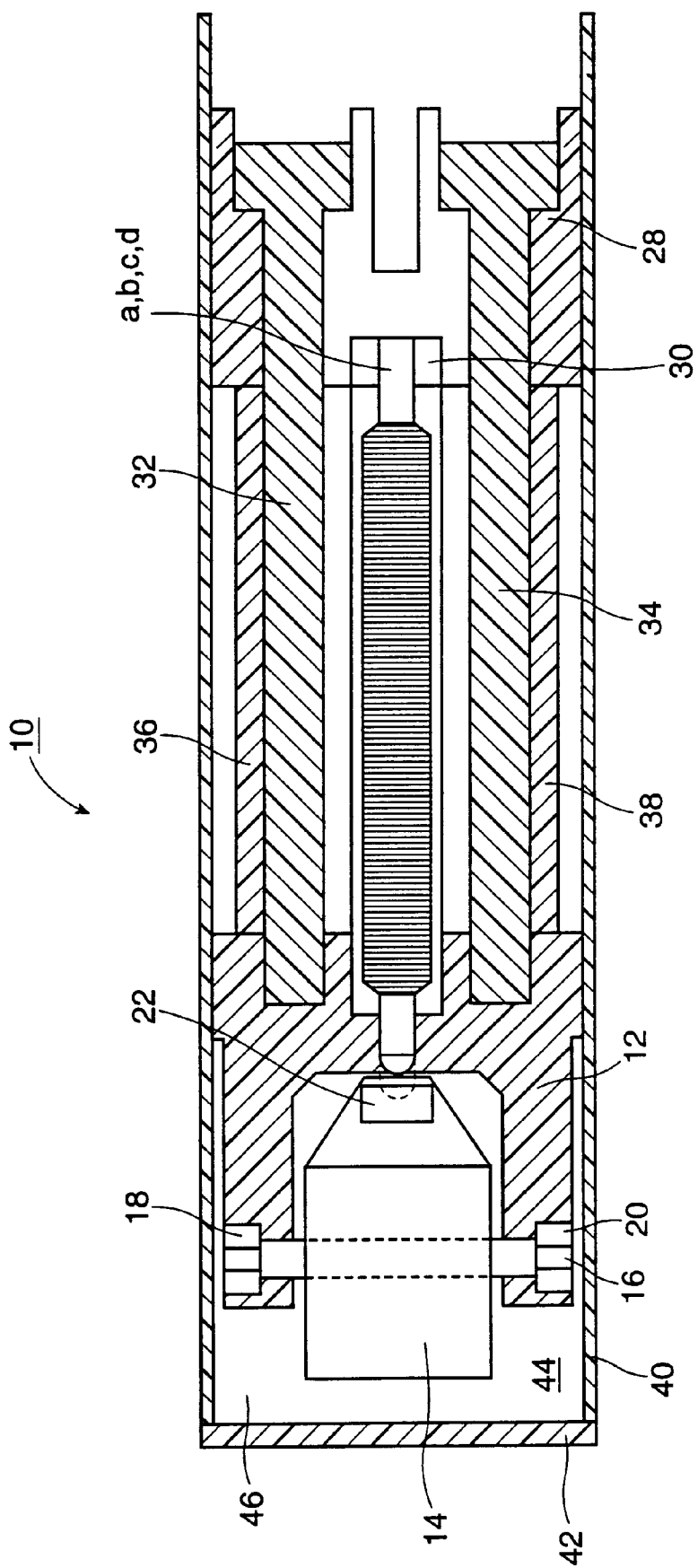
FIG. 3 is a vertical section through the centre of the scanning apparatus of FIG. 1.

Turning now to FIGS. 1, 2, and 3, there is shown a basic ultrasonic scanner according to the present invention. However, it should be noted that, throughout the following discussion, the same reference numerals are utilized to identify identical elements, in varying embodiments of the present invention.

In FIG. 1, the housing and acoustic window components which are shown in FIGS. 2 and 3, have been omitted for purposes of clarity.

A first embodiment of a scanning apparatus in keeping with the present invention is an ultrasonic scanner 10.

There is a front stator assembly 12, containing an ultrasonic transducer 14 mounted on an axle 16 with bearings 18 and 20. A permanent magnet 22 is mounted at the rear of transducer 14. Collectively, transducer 14, axle 16, and permanent magnet 22 are referred to as the rocker. Two permanent magnets 24 and 26 are mounted at the sides of the front stator assembly; these are the rebound magnets. There is also a rear stator assembly 28, containing a ferromagnetic flux return plate 30, to which the ferromagnetic cores of two or more electromagnets (four in this particular case, indicated at "a", "b", "c", and "d" in the Figures) are affixed. The front and rear stator assemblies 12 and 28 are rigidly attached to one another by means of bolts 32 and 34, and cylindrical spacers 36 and 38. Collectively, components 12, 28 and 32, 34, 36, 38 inclusive, are referred to as the frame. The entire assembly is enclosed in a tubular housing 40, the front of which is sealed with an acoustically transparent "window" 42. As seen particularly in FIGS. 2 and 3, the rocker 14, 16, 22, and the ends of the electromagnets a, b, c, d, which extend past the front stator assembly 12 are in a chamber 44, which is a liquid-tight chamber defined at its outer end by the acoustic window 42. The chamber 44 is entirely filled with an acoustic coupling fluid 46 (e.g. Dow Corning Corp. No. 704 diffusion pump oil), which also serves as a lubricant. The rear of the housing must also be closed and sealed in a manner which permits egress of the wire connections to electromagnets a, b, c, d and transducer 14.

The permanent magnets 22, 24, and 26 are cylindrical, and magnetized along the cylinder axis. FIG. 2 illustrates that the respective magnetic vectors are oriented so that the rebound magnets 24 and 26 tend to repel the end of magnet 22 which is furthest from the axle 16, and hence to prohibit the rocker 14 containing the magnet 22 from rotating about axle 16 more than a certain angle from the central position (approximately 37 degrees, in this particular case). The specific magnetic pole indications N (north) and S (south) in FIG. 2 are for illustration only; it should be realized that interchanging N and S for all three permanent magnets will yield the same overall effect.

In operation, a digital electronic control circuit (not shown) switches direct current to the electromagnets a, b, c, d, one (and possibly two) at a time, such that each energized electromagnet tends to attract the rearmost pole of permanent magnet 22. Thus, the rocker tends to tilt to align the magnet 22 with the currently energized electromagnet(s). The flux return plate 30 couples the far end of each energized electromagnet with the ferromagnetic core of its un-energized neighbors, providing a return path for the magnetic flux. To effect repeated back-and-forth rotation of the rocker, the electromagnets are energized in alternating sequence, e.g. first a, then b, then c, then d, then c, and so on; or as noted above, a+b, then b+c, then c+d, then b+c, then a+b, and so on, indefinitely until the source of direct current, or the digital electronic control circuit, is turned off.

The control circuit may be constructed in a variety of ways according to widely known principles of digital electronics. Preferably, the control circuit uses a microprocessor and saturating transistors for current switching.

Figure 4:
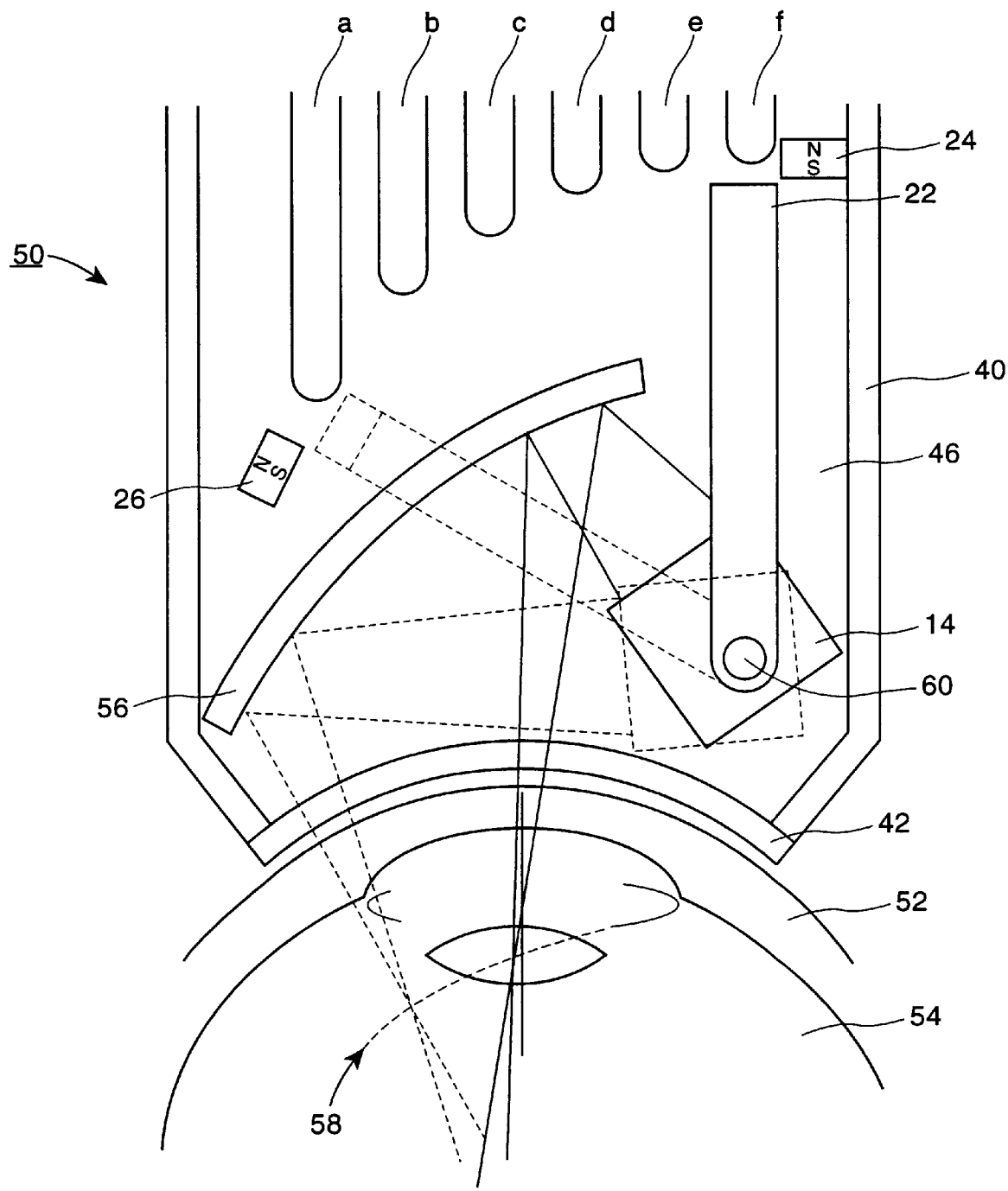
FIG. 4 shows a simplified plan view of a first alternative embodiment of scanning apparatus in keeping with the present invention.
Figure 5:
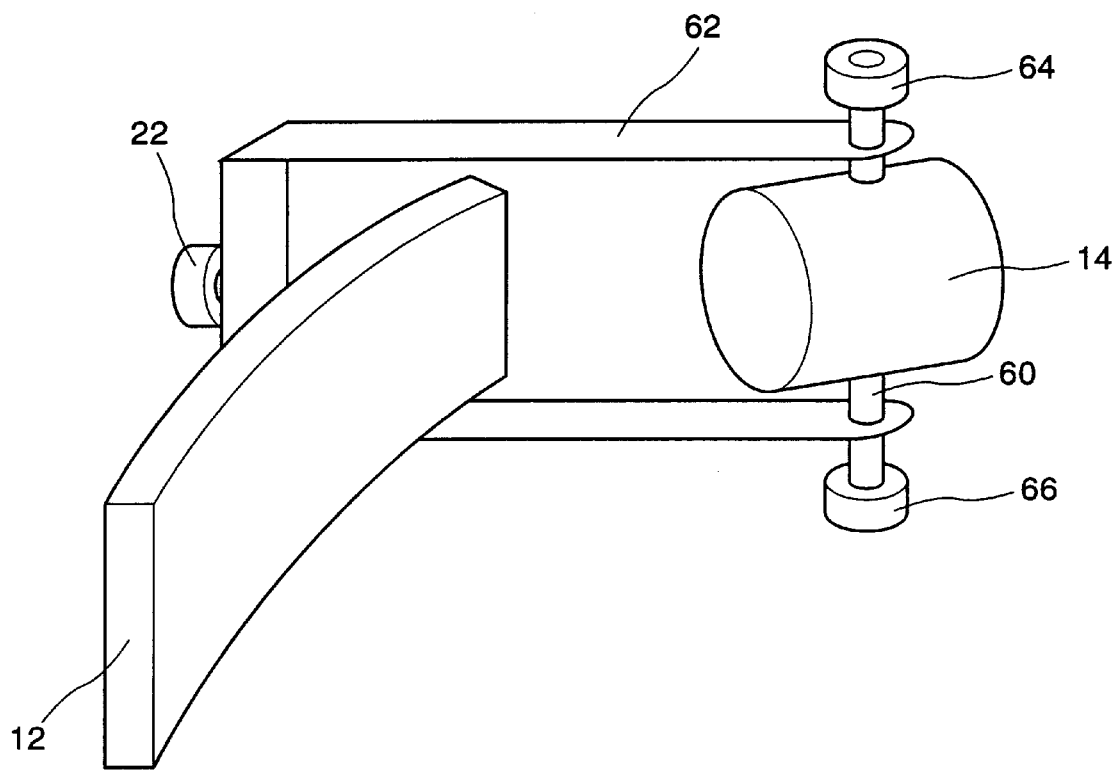
FIG. 5 is a simplified perspective view of the scanning apparatus of FIG. 4.

Turning now to FIGS. 4 and 5, there is illustrated an alternative embodiment of the basic invention, intended for ultrasonic imaging of the anterior segment of the human eye. There is again a tubular housing 40, filled with an acoustic coupling fluid 46, sealed at the front by means of an acoustically transparent "window" 42, and at the rear in any manner which permits egress of the various electrical connecting wires. The acoustic window 42 is concave in this case, so as to match the convexity of the eye-lid 52 and underlying eye 54.

In order to visualize the curved anterior surfaces of the eyelid 52 and eye 54 by means of ultrasonic echography, it is desirable that the beam of acoustic energy emitted by the transducer 14 be kept substantially perpendicular to the curved surfaces, as it is swept to create the ultrasound image. It should be noted that this issue may be of less concern for the probe design illustrated in FIGS. 1 through 3, which is intended for imaging the posterior segment of the eye, whose curvature is compatible with a simple pivoting ultrasound source.

In the embodiment shown in FIGS. 4 and 5, ultrasound imaging is accomplished by means of a pivoted transducer 14, directed backward (with respect to the target eye) toward a fixed, curved acoustic reflector 56. As FIG. 4 shows, this establishes a reversed sector scanning pattern in which the apex of the sector is deep within the eye 54, and preferably the point of focus of the acoustic beam sweeps along a curved line 58 passing through the center of the anterior chamber of the eye.

Specifically, the transducer 14 is attached rigidly to an axle 60 and a U-shaped arm 62, to which is affixed a permanent magnet 22. Collectively, components 14, 60, 62 and 22, are referred to as the rocker. The rocker oscillates within a frame (omitted in FIGS. 4 and 5 for clarity), which is fixed with respect to the housing 40, and more importantly, with respect to the target eye 54. Axle 60 is mounted to the frame by means of the bearings 64 and 66 which permit it and the rocker to rotate. The curved acoustic reflector 56 is mounted rigidly to the frame. A linear array of electromagnets (six are shown in the figure, indicated at a, b, c, d, e, and f) are also mounted rigidly to the frame as shown, along with two permanent magnets 24, 26, oriented so as to repel the rear end of magnet 22 and thus cause the rotor to rebound rather than overshoot the outermost electromagnets.

The electromagnets "a" through "f" inclusive consist of wire coils around cylindrical ferromagnetic cores, linked at the rear by a flux return plate (omitted in FIGS. 4 and 5) substantially similar to that illustrated in FIGS. 1 through 3. It should be realized that the precise number of electromagnets is largely unimportant, though at least two are required for stable operation, and larger numbers minimize the effect of torque ripples, according to principles which are well known in the field of electric motor design. In practice, the electromagnets are made as small as practicable, and the largest number which can fit into the available space is used. As in the previous embodiment, the electromagnets are energized in alternating sequence by means of a digital current-switching control system, causing the rocker to oscillate.

Figure 6:
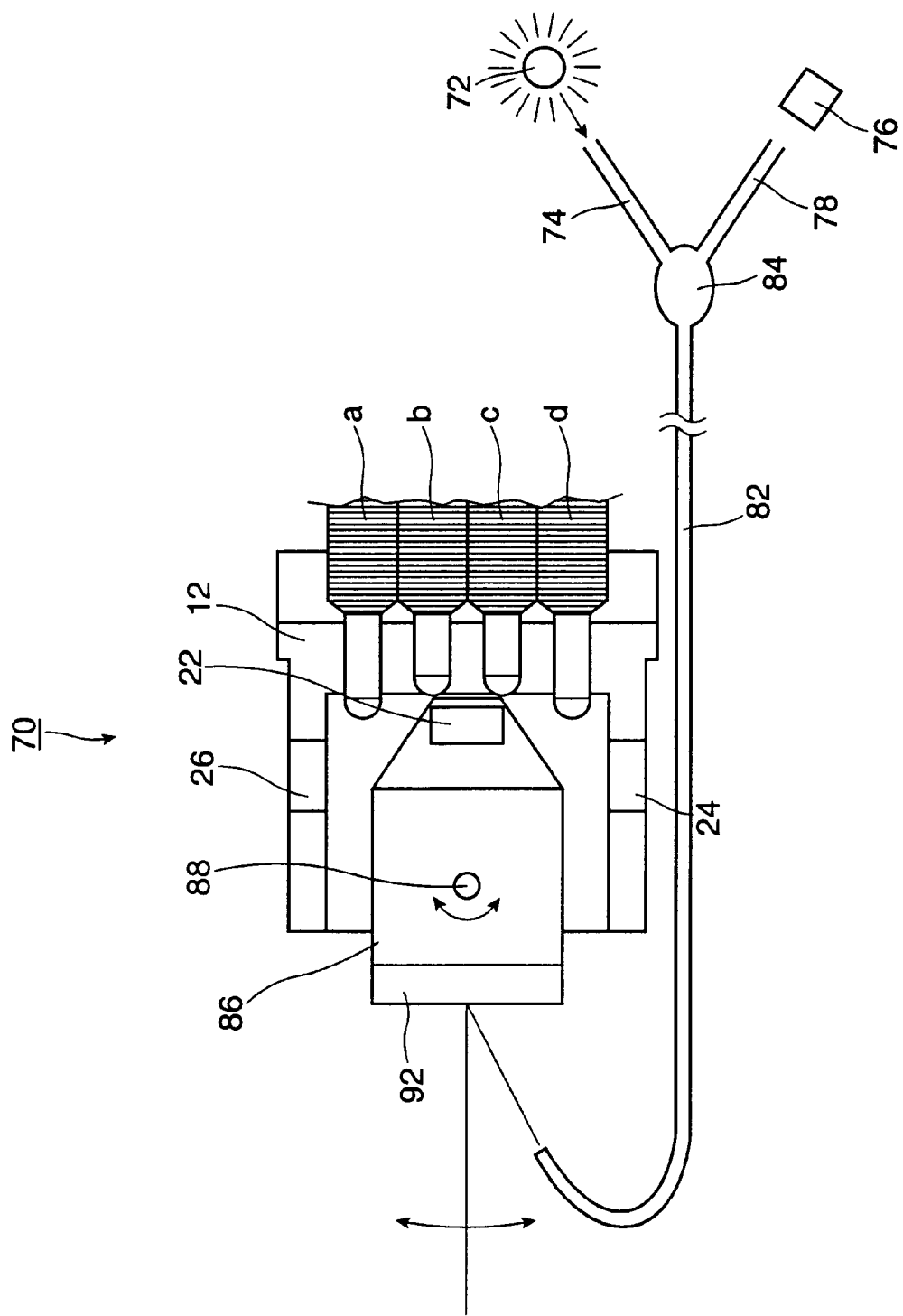
FIG. 6 is a simplified plan view of yet a further embodiment of scanning apparatus in keeping with the present invention.
Figure 7:
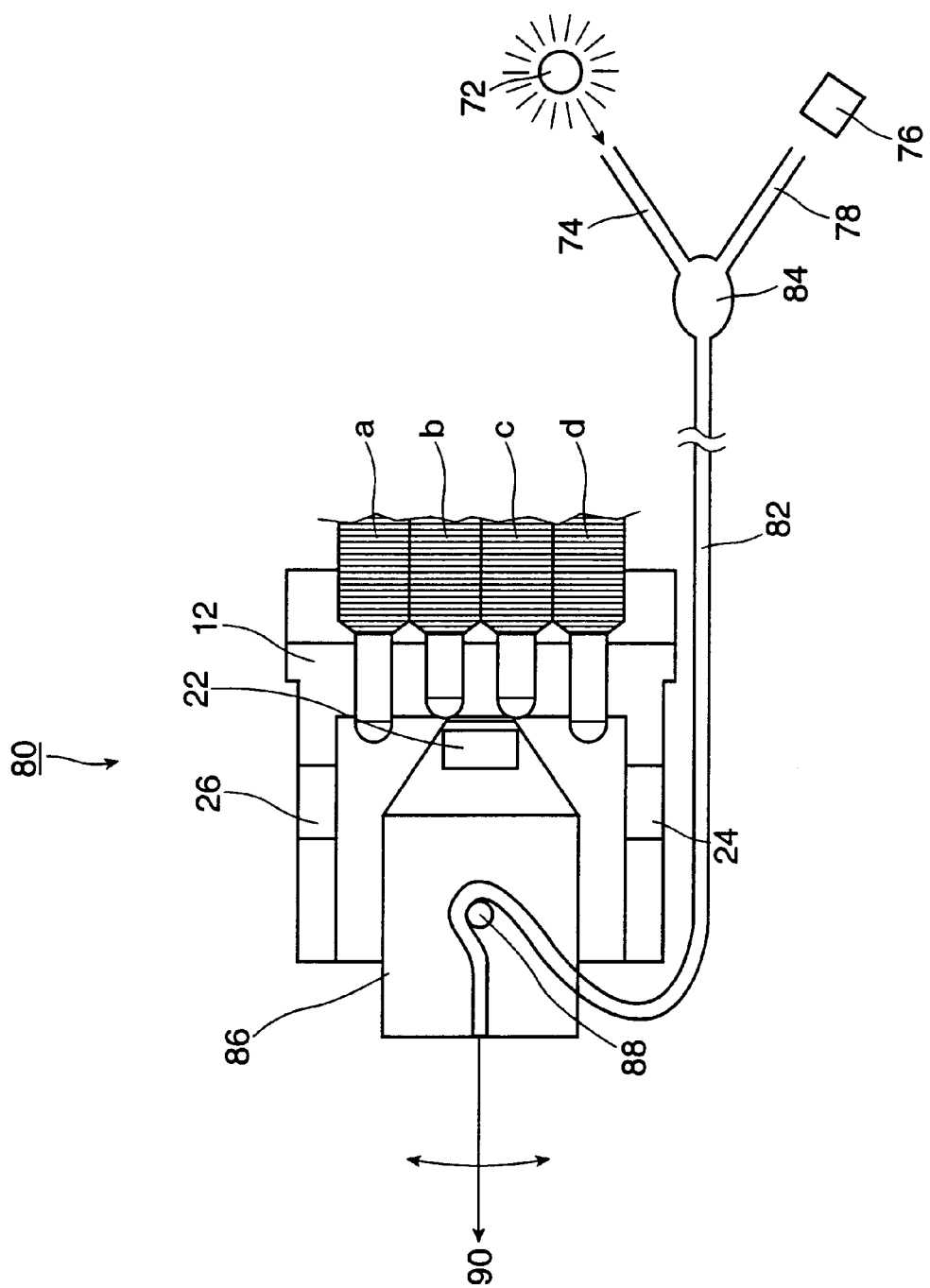
FIG. 7 shows a variation of the embodiment of FIG. 6.

Referring now to FIGS. 6 and 7, there are illustrated further variations 70 and 80, respectively, of the present invention, in which a beam of light is to be swept across a target area, rather than a beam of sound. In both embodiments the light is emitted by a source 72, which is preferably a semiconductor laser diode or superluminescent diode, but the specific type of source is irrelevant to the present invention. The source 72 is coupled to an optical fiber 74. There is also an optical detector 76, preferably a semiconductor type but the specific type is irrelevant, coupled to a second optical fiber 78. Fibers 74 and 78 are coupled to a third fiber 82, through which light is both emitted and received, by means of an optical fiber coupler 84.

Also in both embodiments 70 and 80, there is a rocker 86, mounted on an axle 88, containing a permanent magnet 22, mounted for pivoting motion to a frame 12 to which are also affixed two permanent magnets 24 and 26 (serving as rebound magnets as earlier described), and at least two electromagnets (four shown in the Figures at a, b, c, and d). The entire assembly of the components shown in FIGS. 6 and 7 functions in the same manner as earlier described, together with a digital control circuit to effect oscillatory motion of the rocker.

Also in the embodiments of FIGS. 6 and 7, the purpose of the apparatus is to cause the light from the source 72 emitted from the end of optical fiber 82, to sweep across a target 90, and simultaneously, to direct light reflected back from the target into the end of optical fiber 82 and thence to the detector 76. In the version of the apparatus shown in FIG. 6, an optical mirror 92, preferably a first-surface mirror, is affixed to the front of the rocker 86, and the optical fiber 82 is mounted rigidly with respect to the frame 12, such that its end is directed generally backward with respect to the target 92, toward the mirror 92. Oscillation of the rocker and mirror then causes the reflected light emitted from fiber 82 to sweep the target 90, with reflected light returning to fiber 78 along the reverse path.

In the version of the apparatus shown in FIG. 7, the end of optical fiber 82 is itself rigidly affixed to the rocker 86 and is directed generally forward toward the target 90. Oscillation of the rocker 86 thus directly changes the orientation of the end of fiber 82 through which light is emitted and received.

FIGS. 6 and 7 are intended to illustrate generically, straightforward variations of the present invention, by which a beam of light in an optical imaging system, rather than a beam of sound in an ultrasonic imaging system, may be swept across the target to be imaged in a repeatable and controlled fashion. A large number of substantially similar optical imaging systems are known, involving small variations of the type, number, and configuration of source(s) and detector(s), all of which require a scanning means which is the primary object of the present invention. Specifically, it should be realized that minor variations of the apparatus shown in FIGS. 6 and 7 may be made, according to principles known to those skilled in the art of photonics, to produce reflective, fluorescence, confocal, or interferometric imaging systems, as well as hybrid systems operating according to more than one optical principle. In any case the object of the present invention applies without limitation.

Figure 8:
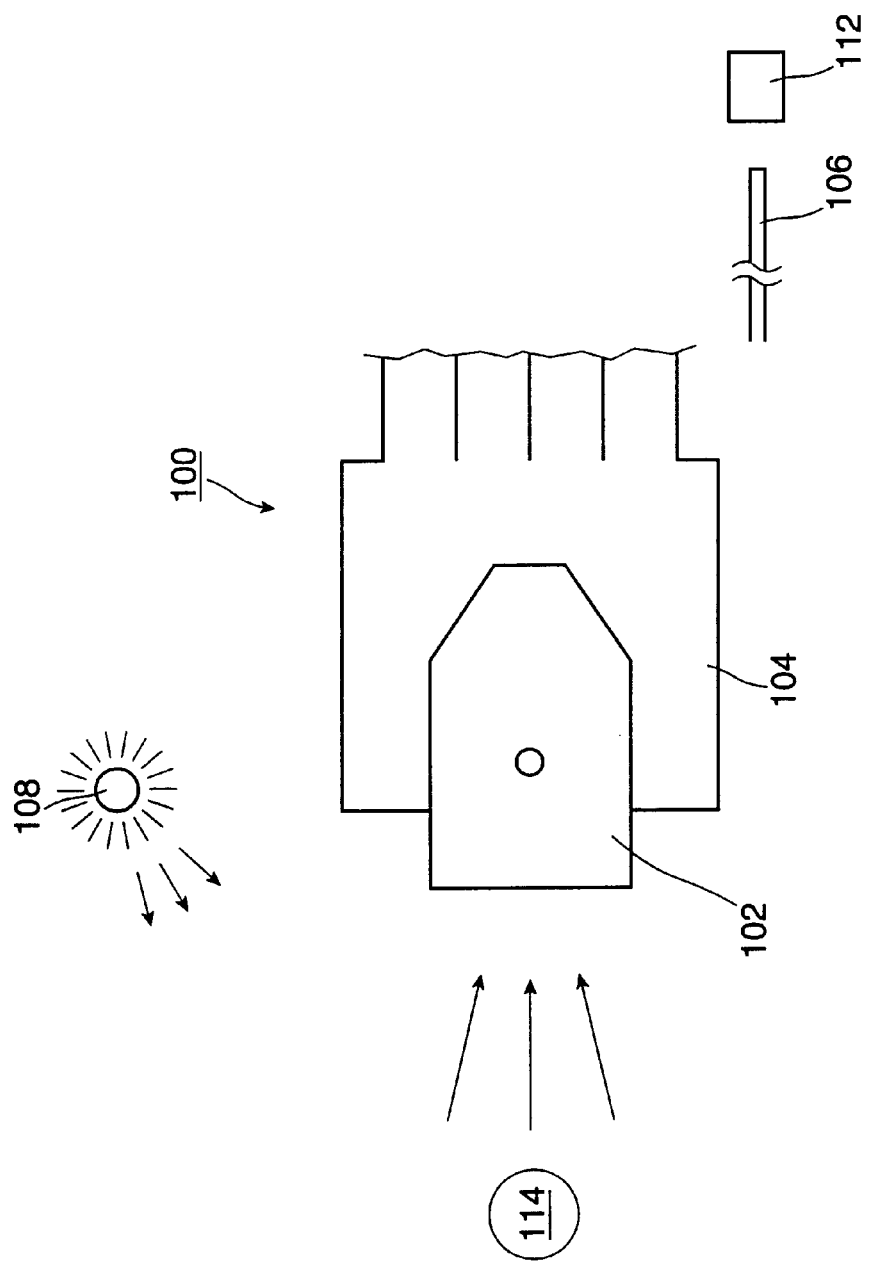
FIG. 8 shows yet a further variation of a scanning apparatus in keeping with the present invention.
Figure 9:
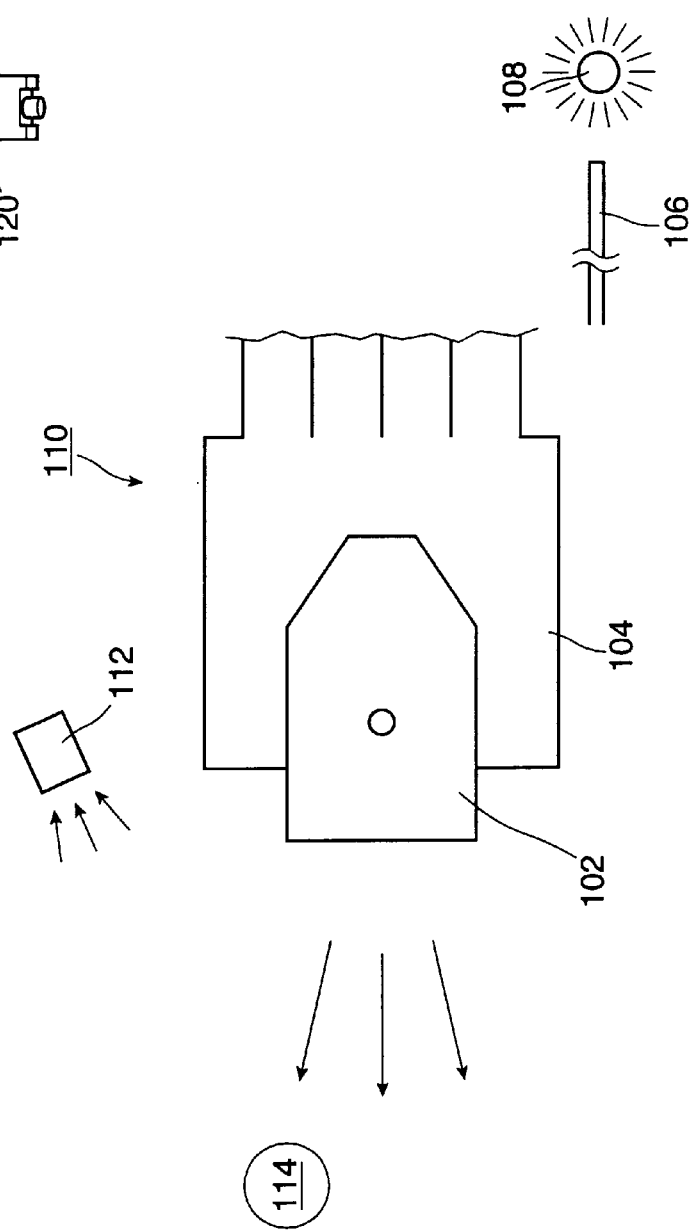
FIG. 9 is a variation of the embodiment of FIG. 8.

Indeed, FIGS. 8 and 9 serve as cases in point with respect to the foregoing. In both of these embodiments 100 and 110, respectively, there is a scanner assembly consisting of a rocker 102 and frame 104 (and other components as previously described, omitted for clarity in those Figures) according to the present invention, and also an optical fiber 106, light source 108 and detector 112. In both embodiments the fiber 106 is linked to the rocker 102 either optically by means of a mirror, as shown in FIG. 6, or mechanically, as shown in FIG. 7. (For clarity, the specific linkage is omitted in the figures.)

FIG. 8 illustrates the case where the source 108 is a non-coherent type (such as an incandescent or gas-discharge lamp) mounted rigidly with respect to the frame 104, and directed generally toward a target 114 in order to illuminate all areas of the target substantially equally, while the effective directional orientation of the detector 112 is swept by means of the scanning mechanism.

FIG. 9 illustrates the opposite case, where the light from the source 108 is swept across the target, and received by a detector 112 (such as a photomultiplier tube), which is mounted rigidly with respect to the frame 104 and capable of receiving light reflected back from the target 114 in substantially any direction.

It should be realized that a sufficiently small optical source or detector could of course be disposed within the rocker of the scanning mechanism, obviating the need for a coupling fiber, and that this does not constitute a significant design variation.

Figure 10:
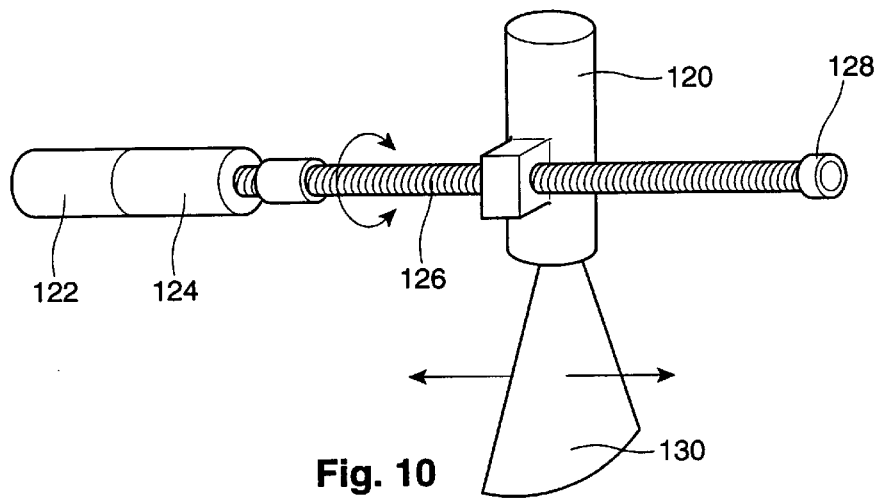
FIGS. 10, 11, and 12 illustrate various manners in which a scanning apparatus in keeping with the present invention may be mechanically coupled to a further mechanism to effect translation, rotation, or tilting, respectively, of a scanning apparatus in keeping with the present invention.
Figure 11:
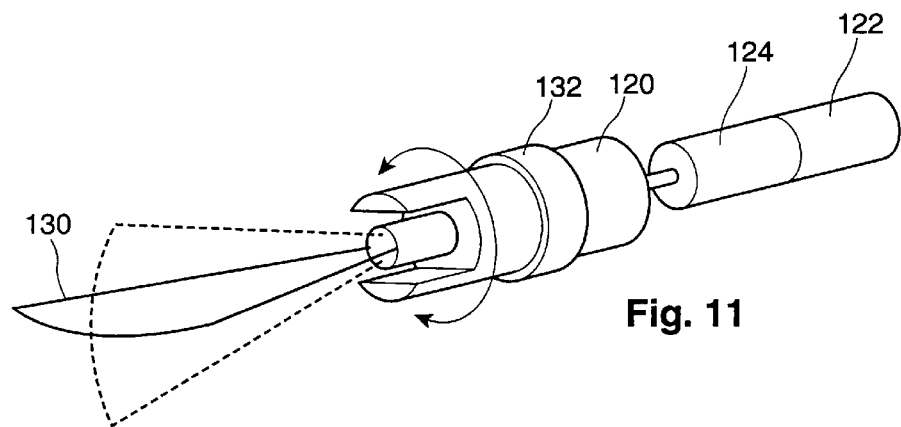
Figure 12:
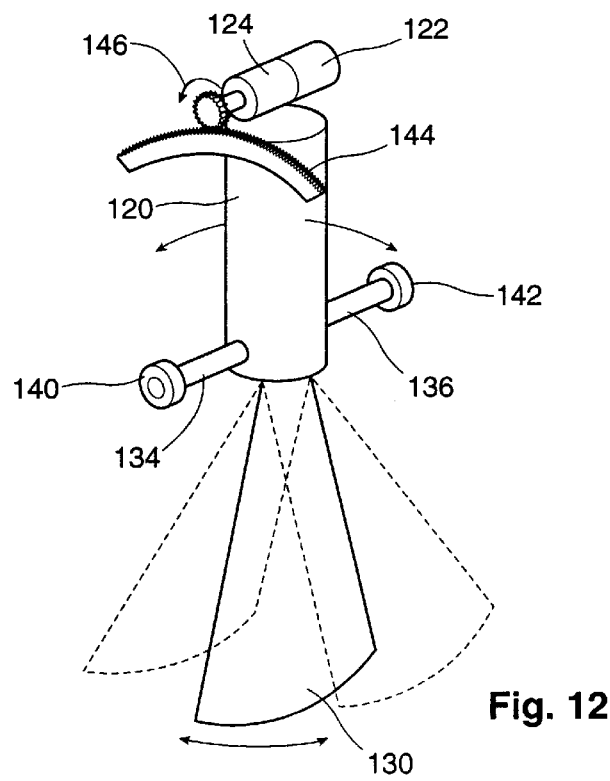

FIGS. 10, 11 and 12 illustrate how the basic sector-scanning mechanism may be augmented for, respectively, translation, rotation, or tilting of the scanning plane, in order to permit three-dimensional tomographic imaging. In all three cases there is a sector scanning mechanism 120, a motor 122 and optionally a reducing gearhead 124, together with some form of mechanical linkage. Also in all three cases, there is a frame and/or housing, omitted in the Figures for improved clarity, whose position and orientation are fixed with respect to the target to be imaged.

FIG. 10 illustrates use of a translational linkage such as a lead-screw 126 and end bearing 128, which serve to translate the plane of sweep 130 along a line substantially perpendicular to the plane. The motor 122 and end bearing 128 are mounted rigidly with respect to a frame (not shown). Techniques for assembling multiple planar images obtained using such an apparatus to produce composite three-dimensional views are well known, and are discussed, in respect of ultrasound imaging, in U.S. Pat. No. 5,842,473, noted above.

FIG. 11 illustrates use of a simple rotational linkage in which the frame of the sector scanner 120 is rigidly attached to the output shaft of the motor 122 (or gearhead 124 if present). The motor 122 is mounted rigidly with respect to a frame (not shown, but which preferably takes the form of a closed tube filled with acoustic coupling liquid, as illustrated in FIGS. 2 and 3). Optionally, a bearing 132 may be provided to constrain the motion of the scanner 120 to pure rotation within the frame. Ultrasonic imaging systems of this type have been described generically in U.S. Pat. No. 5,159,931, noted above, and specific techniques for assembling multiple planar images obtained using such an apparatus to produce composite three-dimensional views have been described in U.S. Pat. No. 5,454,371, noted above.

FIG. 12 illustrates a linkage in which the sector scanner 120 is mounted for tilting motion with respect to a frame. For example, axles 134 and 136, and bearings 140 and 142, together with a partial gear 144 affixed to the scanner 120, are driven by a gear 146 on the shaft 132 of the motor 122 (or gearhead 124, if present). The motor 122, and also bearings 140 and 142, are rigidly mounted to a frame. Ultrasonic imaging systems of this general type have been described, along with specific techniques for assembling multiple planar images obtained using such an apparatus to produce composite three-dimensional views, in U.S. Pat. No. 5,562,095, noted above.

It should be realized that the specific mechanical linkage components shown in FIGS. 10, 11 and 12 are intended to be generically illustrative of their class, and that any type of linkage serving the same purpose should be considered equivalent with respect to the present invention, so long as a sector scanning apparatus in keeping with the present invention, all as previously described, is used. It should also be realized that the motor 122 and gearhead 124 shown in the Figures may similarly be replaced with any means of delivering motive force, including without limitation electric solenoids, hydraulic or pneumatic pistons, rods or cables connected to a physically separate motive mechanism, or direct hand pressure by a human operator, without limiting the applicability of the claims hereto with respect to the sector scanning apparatus being used as a sub-assembly.

Figure 13:
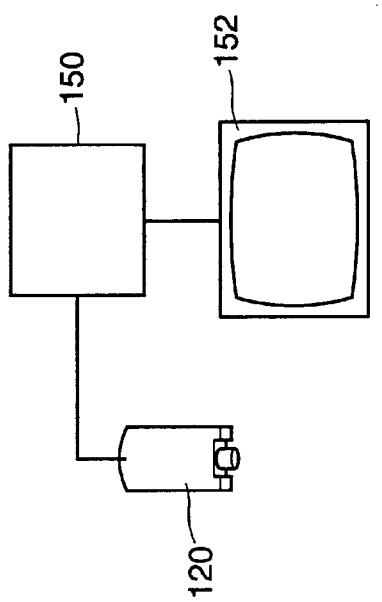
FIG. 13 is a simplified block schematic showing an ultrasound tomographic imaging system which utilizes a scanning apparatus in keeping with the present invention.

Finally, FIG. 13 shows a typical use of any high speed scanning apparatus in keeping with the present invention. However, in this case, a sector scanning mechanism 120 may be an ultrasound scanning apparatus, as contemplated by the present invention, and as described, for example, with respect to FIGS. 1 through 5. The apparatus is used in association with ultrasound image reconstruction circuitry 150, and a display means 152, on which are displayed reconstructed ultrasound images. As noted above, the assembly of ultrasound images is well known, and is outside the scope of the present invention, in any event.

There has been described a high speed scanning apparatus which may have a number of different embodiments, and which may employ a number of different sources of high frequency energy together with appropriate high frequency detectors. However, in each case, the high speed sector scanning apparatus which has been shown and described is one having digital control and is otherwise as specifically defined in the appended claims.

Other modifications and alterations may be used in the design and manufacture of the apparatus of the present invention without departing from the spirit and scope of the accompanying claims.

Throughout this specification and the claims which follow, unless the context requires otherwise, the word "comprise", and variations such as "comprises" or "comprising", will be understood to imply the inclusion of a stated integer or step or group of integers or steps but not to the exclusion of any other integer or step or group of integers or steps.

Moreover, the word "substantially" when used with an adjective or adverb is intended to enhance the scope of the particular characteristic; e.g., substantially perpendicular is intended to mean perpendicular, nearly perpendicular and/or exhibiting characteristics of perpendicularity of one element with respect to another element.

What is claimed is:

1. A high speed sector scanning apparatus having digital control, comprising:
   a frame;
   a rocker mounted on an axle near a first end of said frame, and being adapted for oscillatory movement about a rocker axis defined by said axle through a range of up to 180°;
   a first permanent magnet mounted at the end of said rocker remote from the first end of said frame so as to define a locus which is located in a plane swept by said permanent magnet during oscillatory movement of said rocker;
   at least two electromagnets, each comprising coiled wire wound on an elongated magnetic core, said at least two electromagnets being mounted in said plane swept by said first permanent magnet, each of said at least two electromagnets being constructed so as to have a first end of the magnetic core thereof extending towards said locus defined by said first permanent magnet, whereby magnetic field reaction occurs between said first permanent magnet and at least one of said at least two electromagnets when electric power is selectively applied to said at least one electromagnet at any instant in time;
   a flux return path mounted in said frame and magnetically connected to the ends of said at least two electromagnets;
   digital electrical control means for selectively applying electric power to at least one electromagnet at any instant in time and for sequentially applying electric power to others of said at least two electromagnets over a period of time, whereby magnetic field reaction sequentially occurs between said first permanent magnet and a selected at least one electromagnet so as to cause oscillatory movement of said rocker about said rocker axis as said first permanent magnet moves in said defined locus in said swept plane;
   a source of high frequency energy physically mounted so as to interact with said rocker so that energy is transmitted away from said rocker along a transmission axis of said rocker which is orthogonal to said rocker axis; and
   a detector physically mounted so as to interact with said rocker and so as to detect and receive reflected frequency high energy at the same frequency as the energy from said source, when said reflected high frequency energy is reflected back to said apparatus from an object being scanned thereby.

2. The apparatus of claim 1, wherein the range of oscillatory movement of said rotor about said rotor axis is from 10° up to 95°.

3. The apparatus of claim 2, wherein said source of high frequency energy is an ultrasonic transducer;
   wherein said apparatus further includes an acoustic window at the first end thereof, which acoustic window is acoustically transparent to high frequency energy at the operating frequency of said ultrasonic transducer; and
   wherein said rocker, said transducer, said detector, and said first ends of said at least two electromagnets are sealed in a liquid-tight chamber which is defined at one end thereof by said acoustic window, and said liquid-tight chamber is filled with a liquid which is acoustically transparent to high frequency energy at least within the operating frequency range of said ultrasonic transducer.

4. An ultrasound tomographic imaging system comprising the apparatus of claim 3, together with ultrasonic image reconstruction circuitry and display means for displaying reconstructed ultrasound images.

5. The apparatus of claim 1, further including a pair of permanent rebound magnets mounted in said frame so that one of said pair of permanent rebound magnets is mounted at each end of the locus defined by said first permanent magnet mounted on said rocker, whereby a magnetic repulsion reaction occurs between said first permanent magnet mounted on said rocker and one of said permanent rebound magnets each time said first permanent magnet approaches said respective one of said permanent rebound magnets during oscillatory movement of said rocker.

6. The apparatus of claim 1, wherein each of said source of high frequency energy and said detector is mounted on said rocker, and is chosen from the group consisting of ultrasonic transducers, laser diodes, lamps, light emitting diodes, and superluminescent diodes.

7. The apparatus of claim 1, wherein each of said source of high frequency energy and said detector is physically mounted within said frame;

said apparatus further comprising a curved reflector mounted within said frame near the first ends of said at least two electromagnets, and at least one lever arm extending from said rocker axis of said rocker and having said first permanent magnet mounted on said lever arm at the end thereof remote from said rocker axis;

whereby energy transmitted from said source of high frequency energy is transmitted towards said curved reflector, and is retransmitted from said curved reflector outwardly from said apparatus past said first end of the frame thereof, towards an object to be scanned by said apparatus.

8. The apparatus of claim 7, wherein each of said source of high frequency energy and said detector is mounted on said rocker, and is chosen from the group consisting of ultrasonic transducers, laser diodes, lamps, light emitting diodes, and superluminescent diodes; and wherein said reflector is chosen from the group consisting of sound reflectors and mirrors.

9. The apparatus of claim 1, wherein said source of high frequency energy is a light source physically mounted within said frame, and chosen from the group consisting of laser diodes, lamps, light emitting diodes, superluminescent diodes, and light fibers connected to a light source chosen from the group consisting of laser diodes, lamps, light emitting diodes, and superluminescent diodes;

wherein a planar mirror is mounted on said rocker at an end thereof remote from said first permanent magnet;

wherein said source of high frequency energy is mounted within said frame so as to be directed at said planar mirror;

wherein said planar mirror is orthogonal to said axis of transmission; and wherein said detector is physically mounted in said frame so as to interact with said rocker so as to detect and receive reflected high frequency energy being reflected back to said planar mirror from an object being scanned by said apparatus.

10. The apparatus of claim 1, wherein said source of high frequency energy is a source of broad coverage illumination, wherein said detector is one which detects high frequency energy from said source of broad coverage illumination as it is reflected back to said apparatus from an object being scanned thereby; and wherein said detector is physically mounted on said rocker.

11. The apparatus of claim 10, wherein said source of high frequency energy is a Xenon lamp.

12. The apparatus of claim 1, wherein said source of high frequency energy is a light source physically mounted within said frame, and chosen from the group consisting of laser diodes, lamps, light emitting diodes, superluminescent diodes, and light fibers connected to a light source chosen from the group consisting of laser diodes lamps, light emitting diodes, and superluminescent diodes;

wherein said source of high frequency energy is mounted on said rocker; and wherein said detector is a stationary broad coverage detector.

13. The apparatus of claim 12, wherein said detector is a photomultipier tube.

14. The apparatus of claim 1, wherein there are n electromagnets, where n is a whole integer having a value of at least 2.

15. The apparatus of claim 14, wherein electric power is sequentially applied by said digital control means to each electromagnet one at a time, and wherein electric power is next applied by said digital control means to an electromagnet which is adjacent to the last electromagnet to have had electric power applied to it, each time the sequence of such application of electric power to said electromagnets changes.

16. The apparatus of claim 14, wherein there are at least four electromagnets, and wherein electric power is applied sequentially by said digital control means to pairs of adjacent electromagnets so that, in successive steps of the sequence of such application of electric power to said electromagnets, one of the respective pairs of electromagnets having electric power applied thereto is the same electromagnet.

17. The apparatus of claim 1, further comprising a mechanism which is mechanically coupled to said frame for selectively translating said frame under controlled conditions from one location to another.

18. The apparatus of claim 1, further comprising a mechanism which is mechanically coupled to said frame for selectively rotating said frame under controlled conditions about a longitudinal axis thereof.

19. The apparatus of claim 1, further comprising a mechanism which is mechanically coupled to said frame for selectively tilting said frame under controlled conditions about a tilt axis therefor, whereby each of said plane swept by said first permanent magnet and said transmission axis of said rocker are tilted about said tilt axis.

* * * * *